United States Patent
Luck et al.

(10) Patent No.: US 11,819,189 B2
(45) Date of Patent: *Nov. 21, 2023

(54) OPTICAL DATA TRANSMISSION IN A WIRELESS POWER TRANSMITTER FOR A SURGICAL ROBOTIC SYSTEM

(71) Applicant: Asensus Surgical US, Inc., Durham, NC (US)

(72) Inventors: Randall L. Luck, Cary, NC (US); Kevin Andrew Hufford, Cary, NC (US)

(73) Assignee: Asensus Surgical US, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/972,464

(22) Filed: Oct. 24, 2022

(65) Prior Publication Data

US 2023/0051171 A1    Feb. 16, 2023

Related U.S. Application Data

(63) Continuation of application No. 16/732,935, filed on Jan. 2, 2020, now Pat. No. 11,523,730.

(Continued)

(51) Int. Cl.
*A61B 1/00* (2006.01)
*A61B 34/30* (2016.01)
(Continued)

(52) U.S. Cl.
CPC ...... *A61B 1/00029* (2013.01); *A61B 1/00149* (2013.01); *A61B 1/04* (2013.01);
(Continued)

(58) Field of Classification Search
CPC .............. A61B 1/00029; A61B 34/30; A61B 2034/301; A61B 46/10; H04B 10/80
(Continued)

(56) References Cited

U.S. PATENT DOCUMENTS

| 9,002,437 B2 * | 4/2015 | Yaroshenko | ........... A61B 17/34 |
| | | | 702/150 |
| 11,523,730 B2 * | 12/2022 | Luck | ................. A61B 1/00029 |

(Continued)

FOREIGN PATENT DOCUMENTS

WO    WO-2017044884 A1 *  3/2017   ......... A61B 1/00149

OTHER PUBLICATIONS

Liang et al; Coil Positioning for Wireless Power Transfer System of Automatic Guided Vehicle Based on Magnetic Sensing; Sep. 2020; MDPI; pp. 1-16. (Year: 2020).*

*Primary Examiner* — Amritbir K Sandhu

(57) ABSTRACT

A wireless power transmission system for a robotic surgical system includes features for optical data transmission. A first component of the surgical system includes a control element, a power transmission element and an optical data transmission element; and a second component of the surgical system including a wireless power receiving element and an optical data receiving element, the second component is removably mountable to the first component. In some embodiments, a barrier such as a surgical drape and/or hermetic enclosure is positioned between the first and second components. In one example, of the components is a robotic manipulator arm and another is a powered instrument removably mountable to the manipulator arm.

18 Claims, 9 Drawing Sheets

Related U.S. Application Data

(60) Provisional application No. 62/787,300, filed on Jan. 1, 2019.

(51) Int. Cl.
*A61B 1/313* (2006.01)
*A61B 46/10* (2016.01)
*H04B 10/80* (2013.01)
*A61B 1/04* (2006.01)

(52) U.S. Cl.
CPC ............ *A61B 1/3132* (2013.01); *A61B 34/30* (2016.02); *A61B 46/10* (2016.02); *H04B 10/80* (2013.01); *A61B 2034/301* (2016.02)

(58) Field of Classification Search
USPC ............................................ 600/102; 398/96
See application file for complete search history.

(56) References Cited

U.S. PATENT DOCUMENTS

| | | | |
|---|---|---|---|
| 2014/0363166 A1* | 12/2014 | Lacovara | G01V 1/226 |
| | | | 398/104 |
| 2017/0065365 A1* | 3/2017 | Schuh | A61B 90/50 |
| 2018/0214167 A1* | 8/2018 | Overmyer | A61B 34/30 |
| 2020/0205641 A1* | 7/2020 | Luck | A61B 46/10 |

* cited by examiner

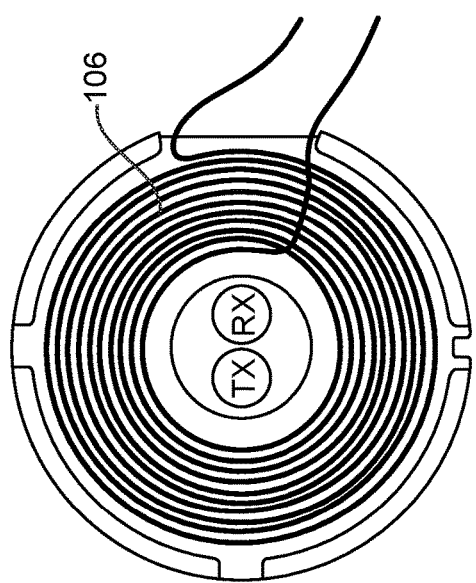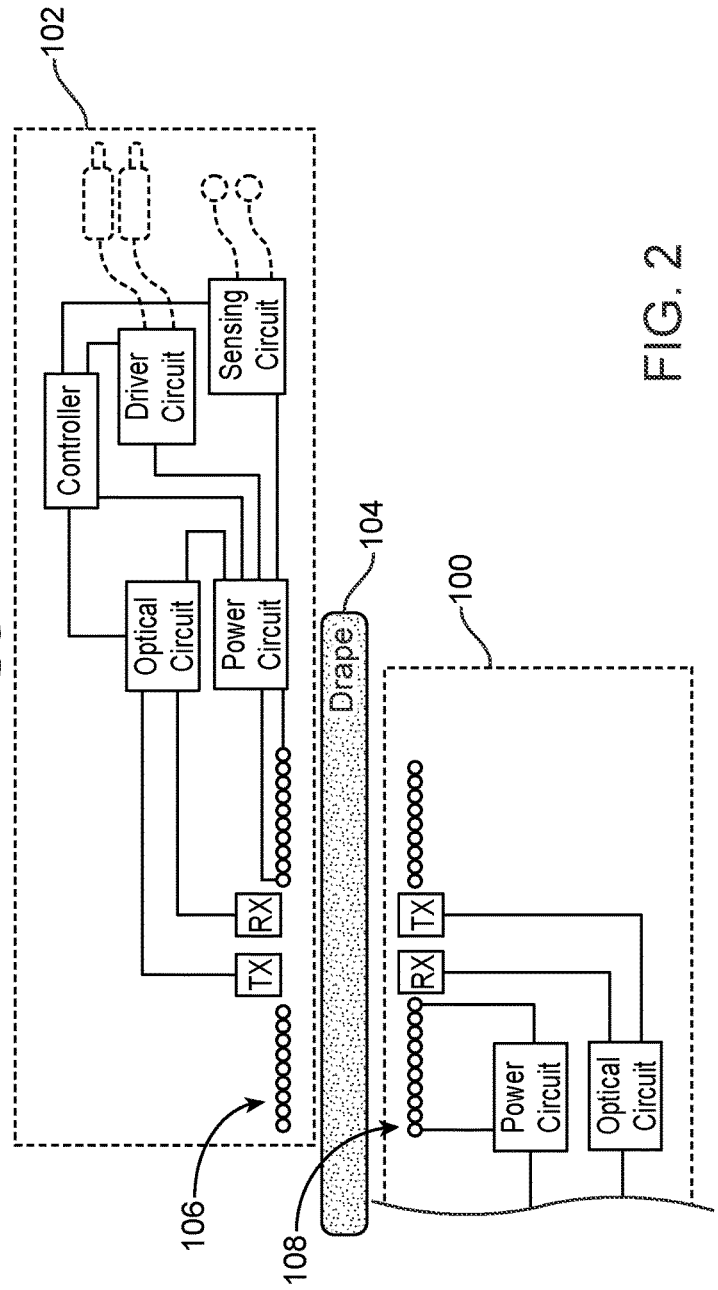

OPTICAL DATA TRANSMISSION IN A WIRELESS POWER TRANSMITTER FOR A SURGICAL ROBOTIC SYSTEM

This application is a continuation of U.S. application Ser. No. 16/732,935, filed Jan. 2, 2020, which claims the benefit of U.S. Provisional Application No. 62/787,300, filed Jan. 1, 2019.

BACKGROUND

Some surgical robotic systems use a plurality of robotic arms or manipulator. Each arm or manipulator carries a surgical instrument, or the camera used to capture images from within the body for display on a monitor. Other surgical robotic systems use a single arm that carries a plurality of instruments and a camera that extend into the body via a single incision. Each of these types of robotic systems uses motors to position and/or orient the camera and instruments and to, where applicable, actuate the instruments, all in accordance with user input. Typical configurations allow two or three instruments and the camera to be supported and manipulated by the system. Input to the system is generated based on input from a surgeon positioned at a master console, typically using input devices such as input handles and a foot pedal. Motion and actuation of the surgical instruments and the camera is controlled by the robotic system controller based on the user input. The image captured by the camera is shown on a display at the surgeon console. The console may be located patient-side, within the sterile field, or outside of the sterile field.

FIG. 12 shows components of a robotic surgical system 10 of the type described in U.S. Pat. No. 9,358,682 and US 20160058513. Features of the system 10 are shown to facilitate an understanding of the way in which the concepts of the present invention may be implemented, but it should be understood that the invention may be used with a variety of different surgical or industrial robotic systems and is not limited to use with system 10.

System 10 comprises at least one robotically controlled arm 11 which operates under the control of a command console 12 operated by the surgeon, as described above. The system described in U.S. Pat. No. 9,358,682 includes a manipulator wrist as part of the distal end of the robotic arm 11. The robotic arm has a distal portion or terminal portion 13 (e.g. at the manipulator wrist in embodiments having such a design) designed to support and operate a surgical device assembly 14. The surgical device assembly includes a surgical instrument having shaft 15 and a distal end effector 17 positionable within a patient 16. The robotic arm is moveable by the system (e.g. in response to user input at the console) to position and orient the surgical instrument within the patient 16.

In this configuration, the robotic arm 11 receives the surgical device assembly 14 at the terminal portion 13 as shown in FIG. 13. The surgical device assembly includes a proximal housing 20 that is received by the terminal portion 13 as shown.

The end effector 17 may be one of many different types of that are used in surgery including, without limitation, end effectors 17 having one or more of the following features: jaws that open and close, a section at the distal end of the shaft that bends or articulates in one or more degrees of freedom, a tip that rolls axially relative to the shaft 15, a shaft that rolls axially relative to the robotic arm 11. For the sake of simplicity, in FIG. 13 the end effector 17 is shown as an oval form in broken lines.

The system includes instrument actuators for driving the motion of the end effector 17. These actuators, which might be motors or other types of motors (e.g. hydraulic/pneumatic), are positioned in the terminal portion 13 of the robotic manipulator, or in the housing 20 of the surgical device assembly, or some combination of the two. In the latter example, some motion of the end effector might be driven using one or more motors in the terminal portion 13, while other motion might be driven using motors in the housing 20.

The robotic arm 11 is typically provided non-sterile. During surgery, it is covered with a sterile drape or barrier 18a as shown in FIG. 13. The surgical instrument (shaft and end effector 15, 17) is provided as a sterile component, and in some cases the housing 20 of the surgical device assembly is also a sterile component and can be mounted directly onto the sterile barrier 18a. In other cases, the housing contains motors or sensitive electronics and thus cannot be subjected to sterilization processes. In those cases, a second sterile barrier 18b such as a sterile bag is positioned around the housing before it is mounted onto the robotic arm. In the configuration described in US 20160058513, once the housing 20 is mounted onto the robotic arm, conductive pins in the housing or the arm are caused to pierce the sterile barriers, creating an electrical connection between components of the arm and electronic components, electromechanical actuators, and/or sensors of the housing 20. This connection allows communication of power used to power the motors within the housing 20.

It is desirable to provide a robotic surgical system that allows power and control data to be provided to a surgical instrument assembly without making any electrical contact. Additionally, feedback of data from the surgical instrument assembly back to the main system is also desirable and is described. Using the embodiments disclosed herein, power transfer and bidirectional data transfer can be achieved without puncturing the surgical drape covering the robotic arm.

BRIEF DESCRIPTION OF THE DRAWINGS

FIG. 1 is a plan view showing optical transmission elements positioned within power transmission/receive coils.

FIG. 2 schematically illustrates a distal part of a robotic manipulator and a surgical instrument assembly mountable on the arm together with a system for wireless power transmission and optical data transfer.

DETAILED DESCRIPTION

Figure 3:
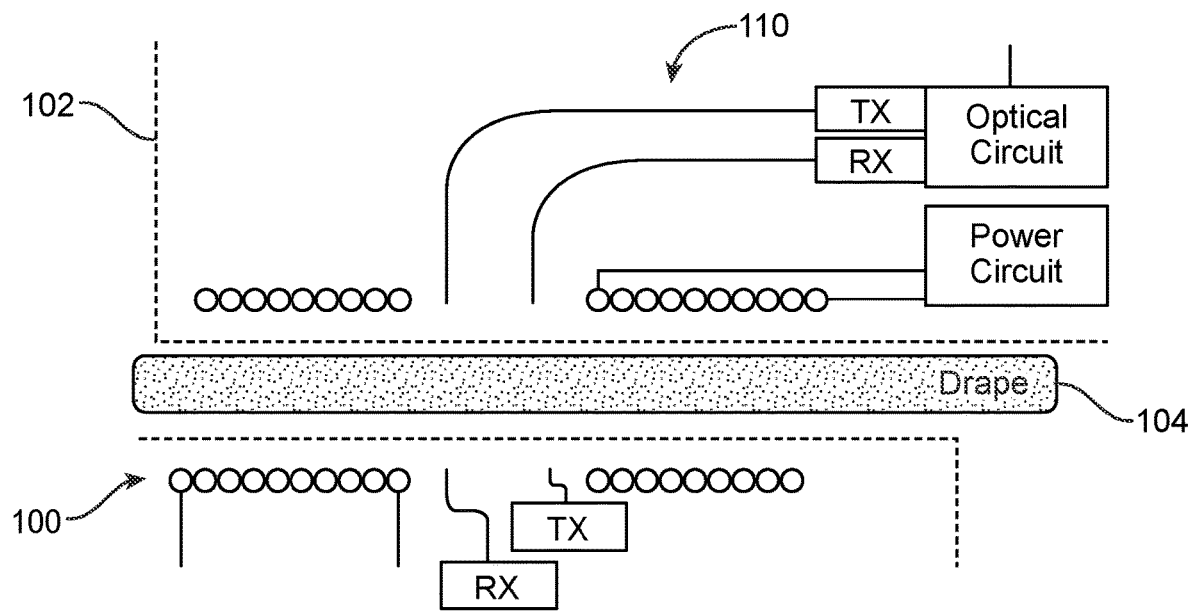
FIG. 3 is similar to FIG. 2 but depicts the use of optical fibers to carry the light between the emitters and detectors.

This application describes configurations that allow powered electronics or active devices to be used on the sterile side of a sterile drape without the need to puncture the drape to provide power or data transmission. As discussed above, current means of power transmission to these devices presents a challenge. In some cases, the drape is pierced to make electrical contact, preventing removal of that instrument mid-procedure. Alternatively, spring-loaded contacts are incorporated into the drape, increasing the cost of the procedure by using more elaborate and thus more expensive drapes.

For these reasons, wireless power transmission across the drape is attractive for providing adequate power for devices while maintaining sterility. It is possible to also transmit data via near-field coils. However, the bandwidth of RF transmission for these coils is somewhat limited, and there are risks of cross-talk between power transmission coils and data transmission coils, or contamination by broad-spectrum RF noise from other equipment such as electrosurgical equipment/electrocautery.

Described below is an optical method of data transmission. The invention provides the ability to communicate data across a sterile barrier/sterile drape wirelessly.

In some implementations, an RF wireless power transmission system is paired with an optical data transmission system.

In some implementations, optical power transmission may also be used (in addition to, or instead of) RF power transmission.

The described configuration is particularly beneficial for use with the type of system described in the Background, in which a surgical device is removably mountable to a robotic manipulator. The instrument may be one of a variety of instruments, such as, but not limited to, a powered surgical instrument, an articulating/wristed surgical instrument, a laparoscopic camera (camera/endoscope, etc.), an illuminator, an OCT probe, a fiber-based spectrometer, an optical or RF tissue-treatment device, an optical tissue interrogator, or an ultrasound probe.

FIG. 2 schematically illustrates a distal part of a robotic manipulator 100 and a surgical instrument assembly 102 mountable on the arm together with a system for wireless power transmission and optical data transfer in accordance with principles described herein. As shown, the system is well suited to a system in which a sterile drape 104 is to be positioned between the surgical instrument assembly and the robotic manipulator. The system includes optical transmit and receive elements TX, RX which, as shown in FIGS. 1 and 2 may be located inside the power transmission and receive coils 106, 108. In other embodiments they are in locations.

Although the application describes bidirectional optical communication, unidirectional optical communication is also within the scope of the invention.

The optical transmission pathway used in the data transmission configuration may be, but is not limited to, LEDs, light pipes, and fiber optic elements.

Figure 4:
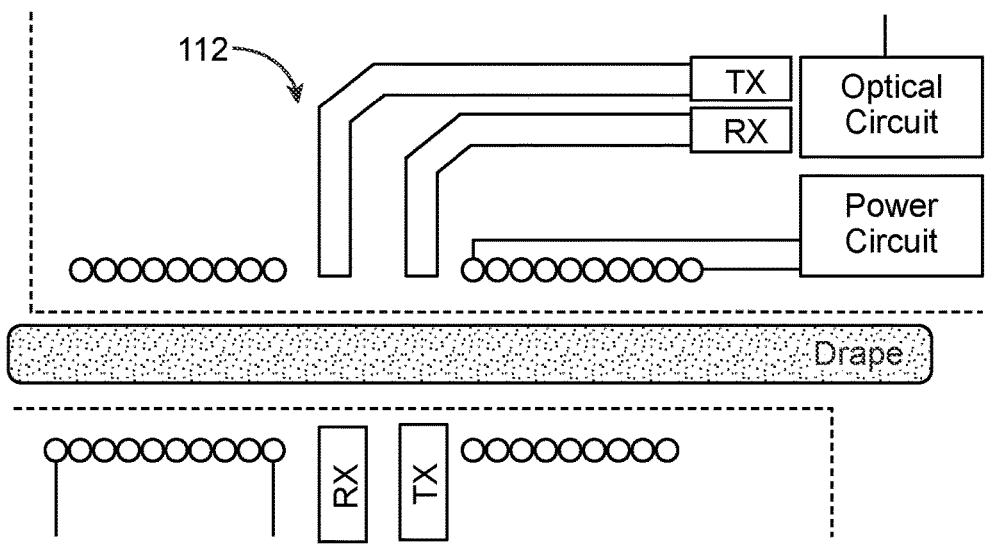
FIG. 4 is similar to FIG. 2, but illustrates the use of light guides to transmit optical energy between emitters and detectors.

FIG. 3 is similar to FIG. 2 but depicts the use of optical fibers 100 to carry the light between the emitter(s) TX and detector(s) RX. This may be combined into a single optical fiber. Lenses, lensing elements, collimators, expanders, beam splitters, light guides, mirrors, prisms, and other optical elements may be added to the optical pathway. In other implementations, the configuration of optical and optical transmission elements may be different on either side of the drape. As an example shown in FIG. 4, light guides 112 may be advantageous for one side of the drape, while fiber optic elements with expanders, or simply the transmitters, may be used on the other side. These may be molded from PMMA (acrylic), polycarbonate, or other suitable plastics. Metallized elements, portions of metallization, reflective film, or other finishing techniques may be added to improve optical performance.

To avoid crosstalk between elements, features may be added to minimize light spill. Suitable features include, but are not limited to: lenses, reflectors, ribs, shielding features/snoots/grids. To allow for proper function in spite of (slight) misalignment between transmitting and receiving elements, a transmit element may have a narrow emission beam angle or be protected by an extended baffle or feature, while a receiving element may have a larger opening or wider lens to still receive the transmitted data.

Figure 5:
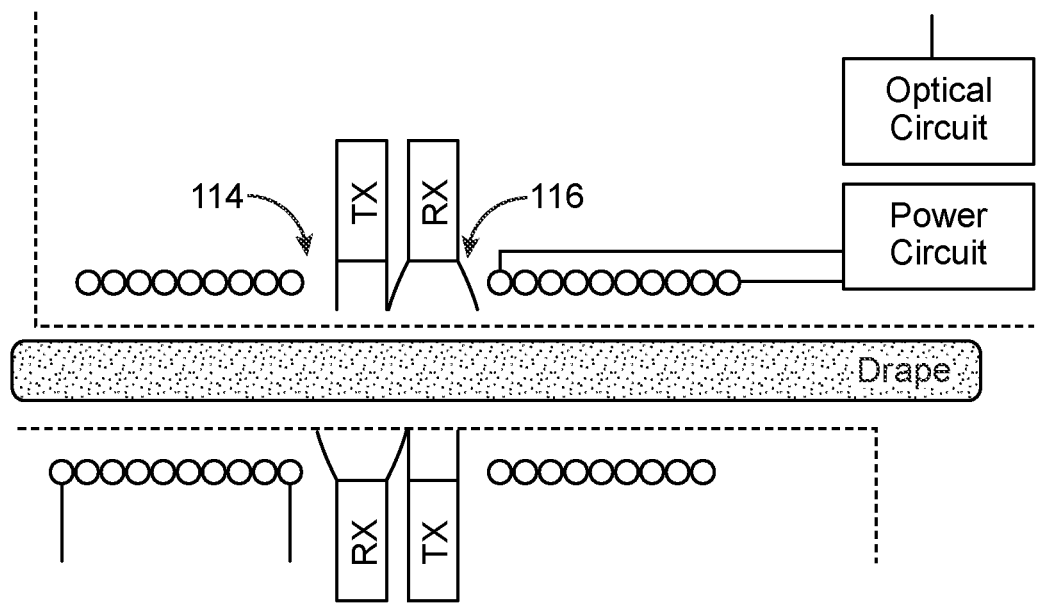
FIG. 5 is similar to FIG. 2, but further illustrates the use of shielding/collimating features and reflectors.

As shown in FIG. 5, optical elements or other design features may be added to improve performance. Shown in this figure are shielding features/collimating features 114 to narrow the beam of the transmitters, while reflectors 116 are positioned allow the receivers to receive data from slightly misaligned transmitters. Other elements may be added to the respective optical paths, and the configurations may be different or asymmetric.

Multiple emitters and/or multiple detectors may be used to improve reliability of transmission and tolerance of misalignment or wrinkles/imperfections in the drape.

Figure 6:
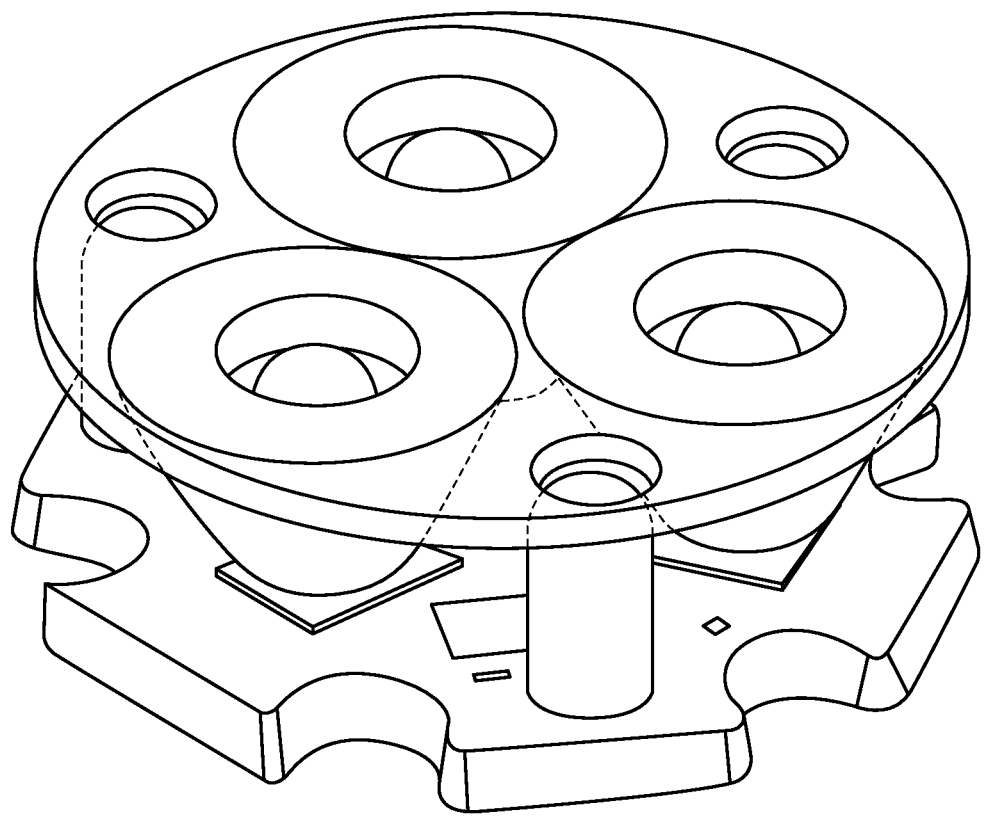
FIG. 6 is a perspective view of a multi-element TIR LED lens which may be positioned in the optical pathway between the emitters and detectors.

FIG. 6 shows a multi-element TIR LED lens, which allows better mixing between adjacent LEDs and may provide better tolerance for misalignment/improve sensitivity if detectors are placed at the base of the optic. This may also be used to provide transmission at various wavelengths of light to improve performance.

Infrared wavelengths transmit more easily through plastic materials, thus in some implementations, infrared wavelengths are used to transmit data. Multiple wavelengths of (infrared) light may also be used. In some implementations, the system may tune the transmitted wavelength(s) and/or intensities or illuminator/detector locations to improve performance. The system may sense reflected light/backscatter from a transmitter or series of transmitters to determine if the pathway is obstructed and adjust the parameters mentioned previously accordingly. If multiple emitters are used, this may be described as pixel-mapping of the optimal optical pathway.

Figure 7:
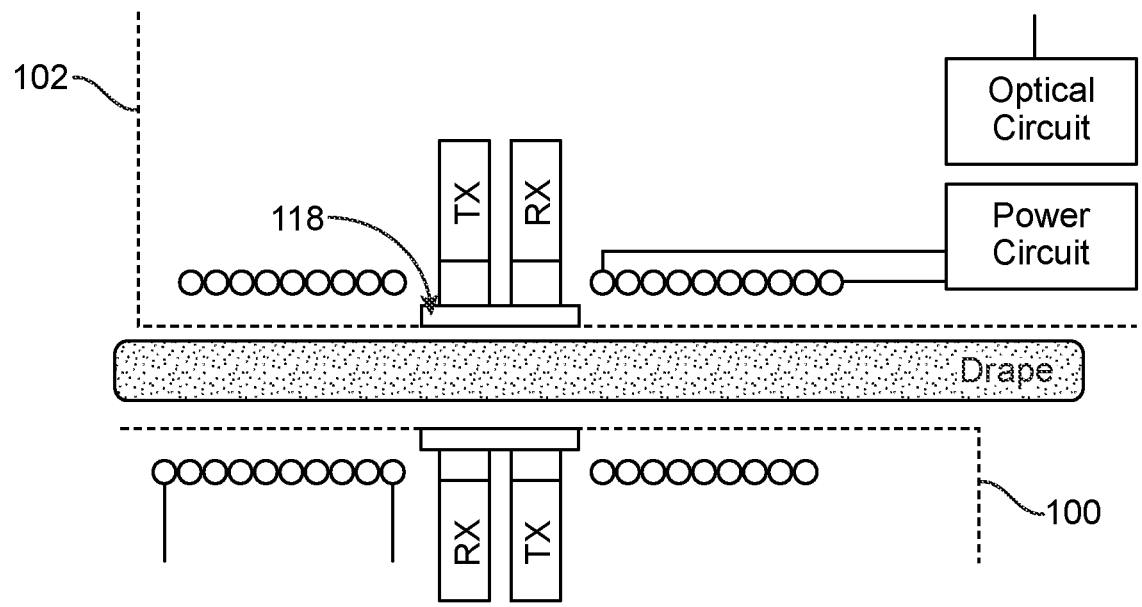
FIG. 7 is similar to FIG. 2 but illustrates the use of hermetic windows to provide a sealed surface for the enclosures containing the electronic components on opposite sides of the drape.

In some implementations, a hermetic window (or set of windows, or optical elements) may be used to allow the light to transmit, while still providing a barrier for sterilization/cleaning. In some implementations, this window is sapphire. In some implementations, this is polycarbonate designed for infrared wavelengths. In some implementations, another material (of an enclosure/structure/frame) is over-molded onto the hermetic window. In some implementations, the hermetic window is over-molded onto the rest of the structure/enclosure. See FIG. 7, in which hermetic window(s) 118 provide a sealed surface for the enclosure(s) of the surgical device assembly 102 and robotic manipulator 100 while allowing optical transmission. However, as (some) infrared wavelengths are able to pass through some plastic materials, a hermetic window may not be necessary.

Filters and/or polarizers may be added to the optical pathway to minimize cross-talk. These may be integrated into a hermetic window, added as a film, or as (a) separate element(s). To minimize cross-talk, the transmit and receive signals may be time-multiplexed. These signals may alternate, or a number of command signals may be transmitted, with occasional updates received from the slave device.

To minimize cross-talk and/or to minimize the number of elements, the signals may be frequency/wavelength multiplexed.

To combine both transmit and detection in the same optical path, a number of optical techniques may be used. One option may be to use a multi-element TIR lens as shown previously. Another option may be to use a beam splitter, dichroic mirror, or light pipe. It also may be possible to position the emitter and detector in close proximity such that the illumination angles are sufficient for coverage.

The same transmission paths for transmit and receive could be used if one direction of dataflow used for example an infrared LED on one side and an infrared sensitive photodiode on the other side, while the other direction of data flow used a visible LED like green or blue on one side and a photodiode sensitive to green or blue on the other side. If this bidirectional optical arrangement was put at the center of the inductive power transfer coil (similar to what is shown in FIG. 1, but with a single element in the middle of the coil) then the system could be made rotationally tolerant. Such a configuration would be particularly useful in providing communication across components that have rotational movement between then. For example, this arrangement is useful in components such as robot joints. In such a case, the joint could then be allowed to freely rotate through 360 degrees.

Figure 8:
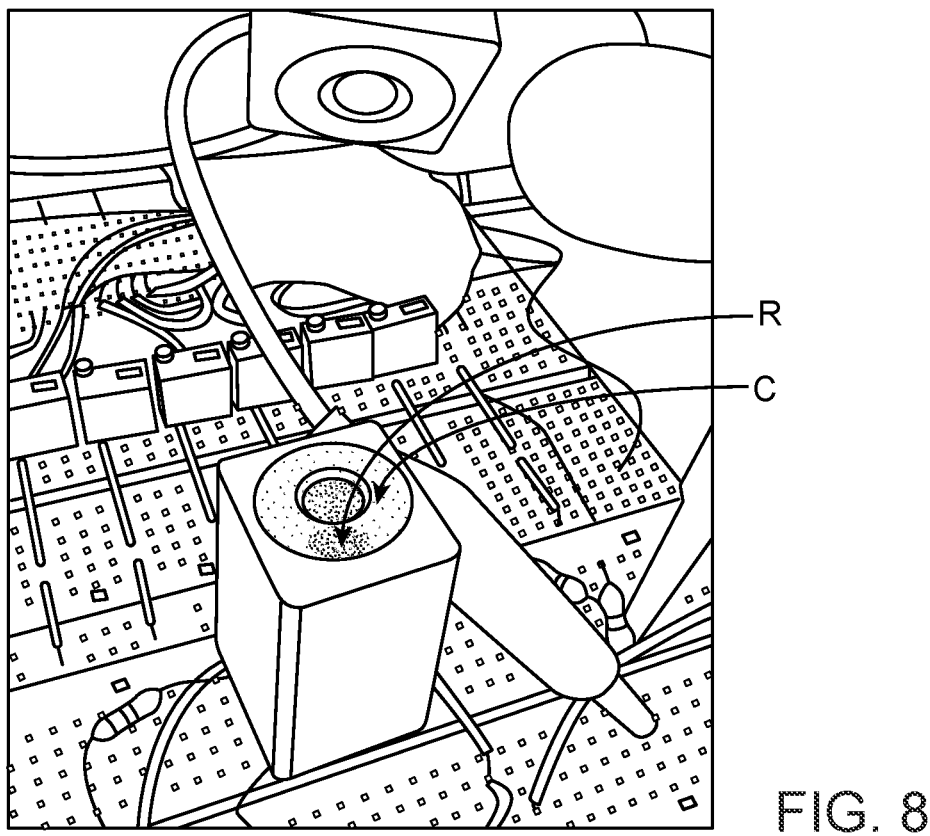
FIG. 8 is a photograph of a test set-up of an optical element of the bidirectional optical data transmission unit.

An alternate implementation of a rotationally-tolerant data optical transmission system configured for bidirectional optical data transmission is shown in FIG. 8. Note that the light from the red LED is contained within the central light pipe/optical path C, while the light from the orange LED is contained in the concentric ring R used as a light pipe/optical path. Both optical paths maintain line of sight throughout rotation about the longitudinal axis. A configuration like this could maintain optical communication across a robotic joint, and/or would also be tolerant of slight misalignment of two mating components.

Figure 9:
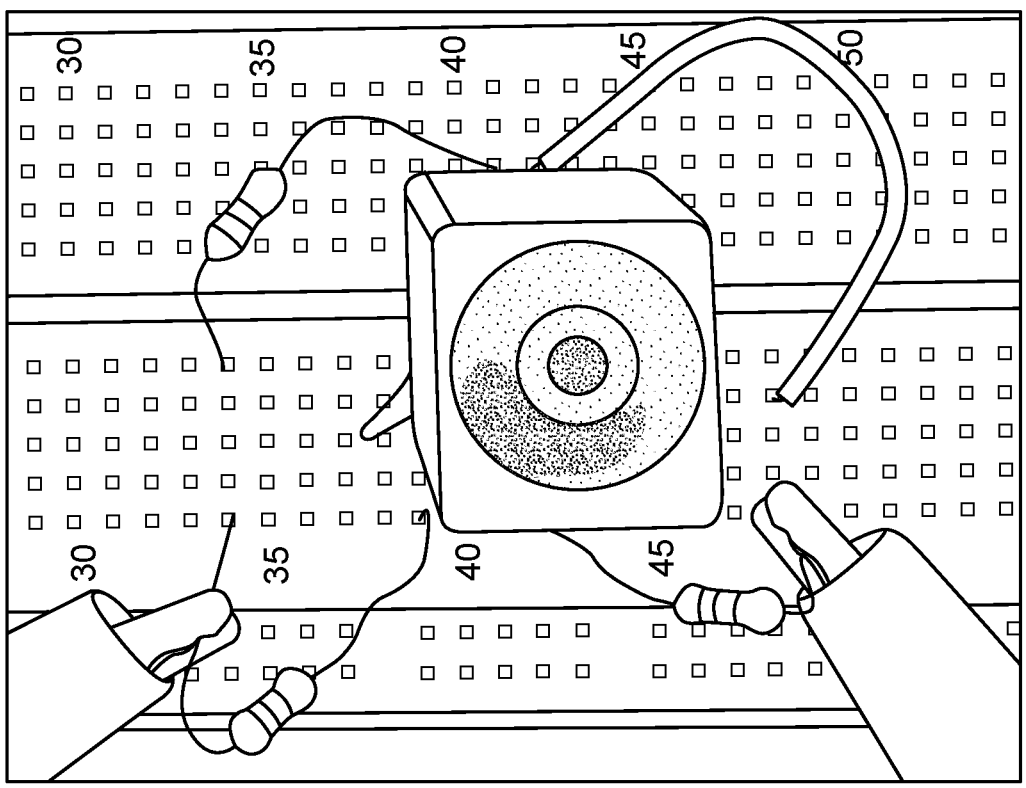
FIG. 9 is similar to FIG. 8, and illustrates the additional use of a second LED or detector to provide illumination around a larger portion of the circular ring.

FIG. 9 shows that a second LED or detector may be used to improve coverage of a circular ring, or an alternate means of diffusion, alternate material, or other coupling means may be used to improve the diffusion/increase the TIR (Total Internal Reflection).

Figure 10A:
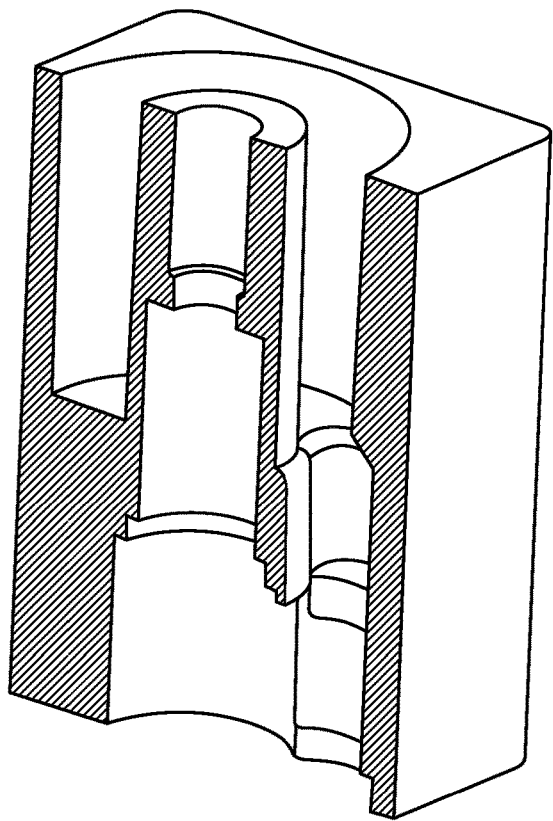
FIGS. 10A and 10B are cross-section views of a concentric optical configuration.
Figure 10B:
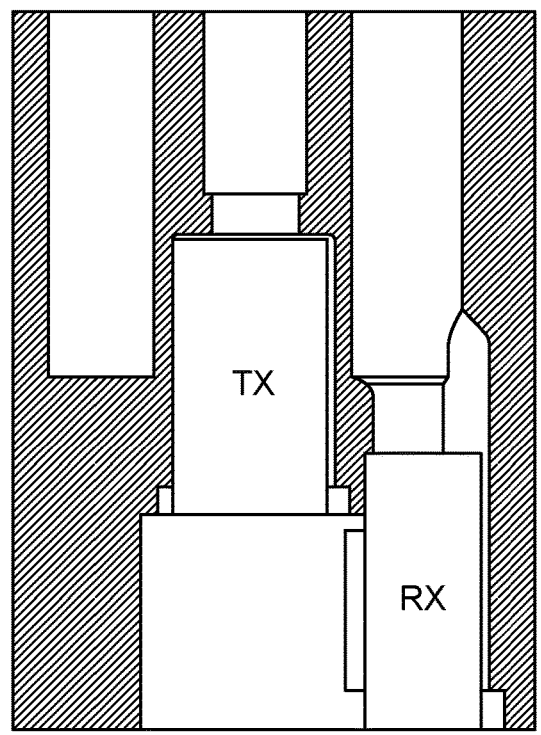

FIGS. 10A and 10B are section views of a concentric optical configuration. In this implementation, a shaft for a rotational joint may serve as a rotational axis, and one or more optical paths may exist as concentric rings about the rotational joint. This may be a passive shaft or an active shaft, such as a motor shaft. This would allow complete rotation of a robotic joint, with bidirectional optical communication occurring with either two concentric rings around that shaft, or as a single concentric ring, with the multi-wavelength approach mentioned previously.

It also should be noted that an inductive data transfer scheme such as described in separately proposed in co-pending, commonly-owned U.S. application Ser. No. 16/051,466, "Contactless Power and Data Transmission for Surgical Robotic System" which is incorporated herein by reference, could be built in a concentric configuration with the larger power coils around the outside and the much smaller data coils in the center. In order to prevent interference with each other, the power and data transfers might be operated at separate carrier frequencies such as 100 kHz for the power and 13.56 MHz for the data. The coils are set up with capacitors to be resonant and this would help with isolating the two frequencies. The data transfer scheme would be half duplex, with only one direction transmitting transmit at a time.

In some implementations, an optical power system may be used to transmit power wirelessly. This may be combined with an RF wireless power transmission system, or it may be standalone in an application with lower-power requirements. This may use an emitter and a detector that generates electrical power from the light energy.

It may be possible to combine the optical data transmission elements with the optical power transmission elements. The optical data may be transmitted as a high-frequency signal on a higher-power optical transmission. An optical detector may collect the fringe light off the photocell used for power.

The pairing of optical power transmission with RF power transmission may provide lower power to some elements (such as control electronics), while higher-power elements (such as motors) may be powered by the RF coils. This may prove advantageous in some applications. For instance, if an application requires that the broadcast RF be minimal, communication with the instrument/end effector would still be possible. Or, if broad-spectrum RF, such as that generated by electrosurgical equipment, interrupts the RF power transmission or reduces its performance, the control electronics would still be powered, and control/feedback from the instrument/end effector would still be possible.

For some applications, optical power transmission may only be able to provide low levels of power, but it may be possible to provide "trickle-charging" of a battery and/or capacitor wirelessly. This may be useful for intermittent transmissions, or for supporting something with low-power and/or intermittent usage. These applications may include an illuminator, a grasper jaw/retractor which may only have infrequent grasp/release usage, a user interface handle (which may have infrequent presses of a button), or any number of other applications.

Figure 11:
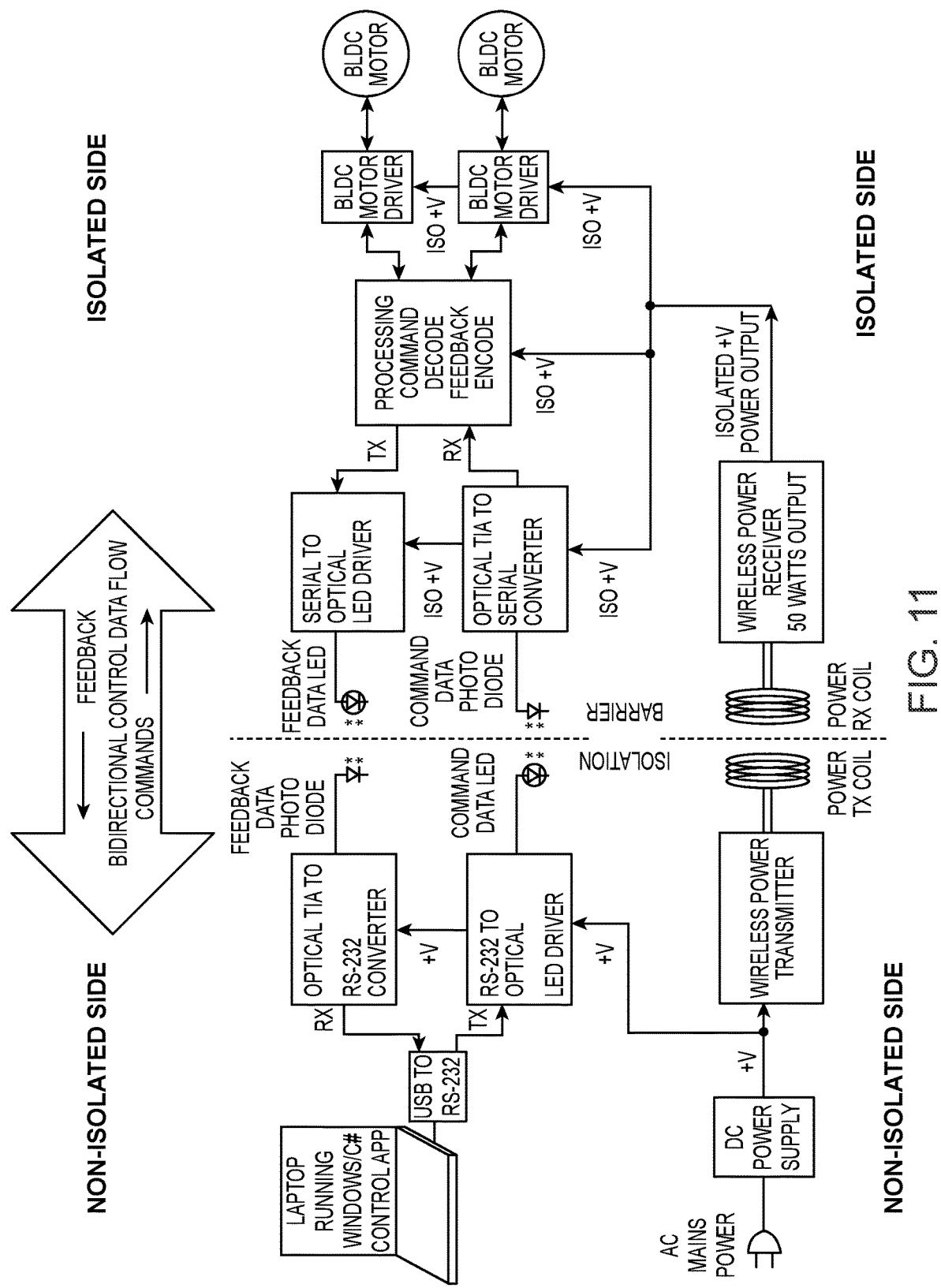
FIG. 11 is a schematic view of a proposed contactless power and optical data transmission system for transmitting power and data across a barrier, such as a surgical drape and/or hermetic enclosures.
Figure 12:
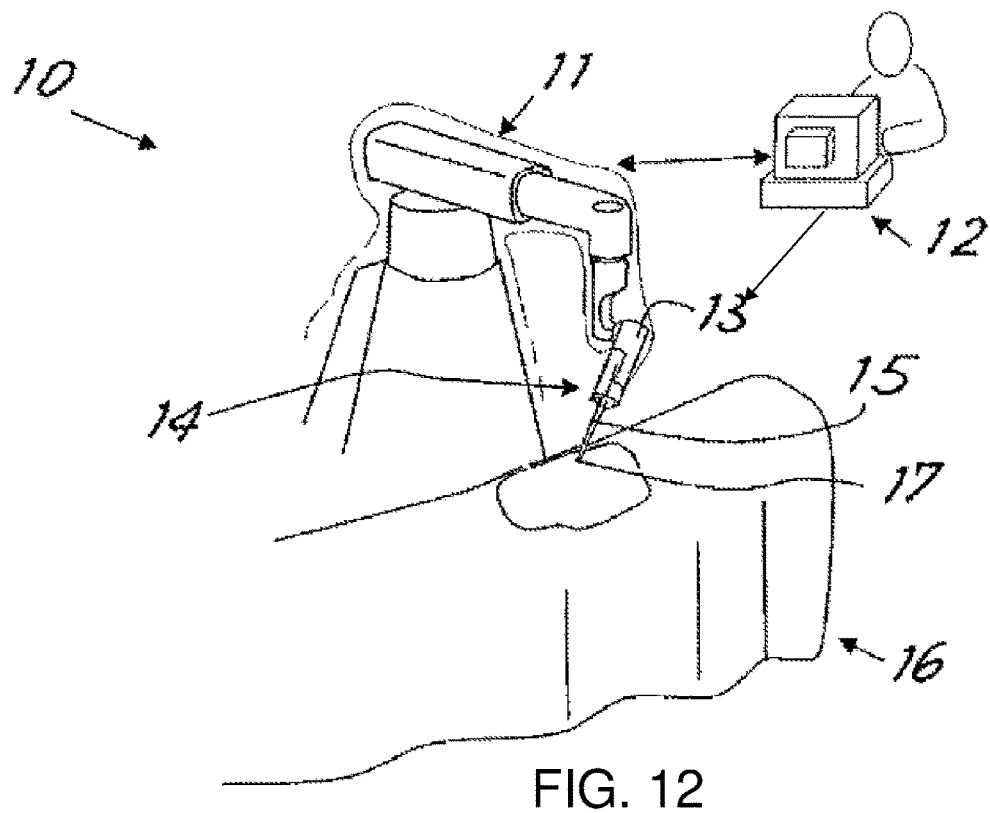
FIG. 12 schematically depicts use of a surgical robotic system to perform surgery on a patient.
Figure 13:
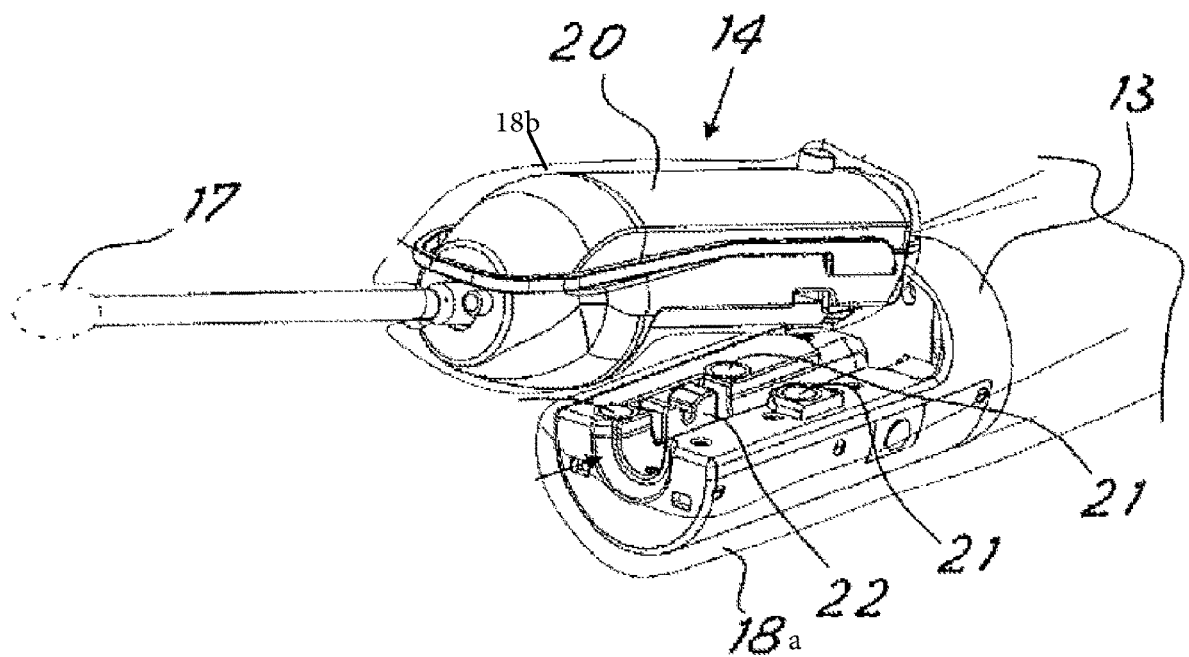
FIG. 13 is a perspective view of a manipulator arm and detachable surgical instrument, which may incorporate the principles described in this application for transmission of data and power.

A schematic view of a proposed contactless power and optical data transmission system is shown in FIG. 11.

The system described in this application has numerous advantages, including the ability to provide contactless, wireless power and data communications from a surgical robotic arm to components of a completely surgical device assembly housing thus preserving the sterile barrier which is important in the operating room. It does so while providing sufficient transmitted power to run the end effector's motors.

It should be understood that while the preferred form of this invention combines wireless transmission of power with optical transmission of control and data information, it should be understood that the system may be modified in certain ways to exclude some features without departing from the scope of the invention. For example, one alternative embodiment might make use only the power transmission features described above. Another might make use only of optical data transmission. These concepts may also be combined with those described in co-pending, commonly-owned U.S. application Ser. No. 16/051,466, "Contactless Power and Data Transmission for Surgical Robotic System" which is incorporated herein by reference.

The described features include a number of novel aspects including, without limitation,
- a. The pairing of optical data transmission with RF data transmission
- b. The use of optical power transmission in addition to RF power transmission
- c. The use of multiple wavelengths The described embodiments provide a number of advantages over existing technology. These include:
- a. Higher bandwidth data transmission using optical energy
- b. Greater robustness to an RF noise environment
- c. Cleaner optical data transmission with "dirtier" RF power transmission All patents and applications referred to herein, including for purposes of priority, are incorporated herein by reference.

What is claimed is:

1. A method of wirelessly powering a surgical device of a robotic surgical system, comprising:
   providing, on a robotic manipulator, a control element, a power transmission element comprising a first coil, said coil defining a first coil center, and a first optical data element disposed in the first coil center; and
   providing, on the surgical device, a wireless power receiving element comprising a second coil defining a second coil center and a second optical data element disposed within the second coil center,
   mounting removably the surgical device to the robotic manipulator,
   transmitting wirelessly power from the power transmission element to the wireless power receiving element to operate a function of the surgical device, and
   transmitting wirelessly optical data between the robotic manipulator and the surgical device.

2. The method of claim 1, wherein the surgical device is a powered surgical instrument.

3. The method of claim 2, wherein the surgical device is an articulated and/or wristed surgical instrument.

4. The method of claim 1, wherein the surgical device is a laparoscopic and/or endoscopic camera.

5. The method of claim 1, wherein the transmitting of the optical data wirelessly comprises unidirectionally transmitting optical data transmission from the first optical data element to the second optical data element.

6. The method of claim 1, wherein the transmitting of the optical data wirelessly comprises bidirectionally transmitting optical data between the first and second optical data elements.

7. The method of claim 6, wherein the transmission of optical data to the second optical data element and the receiving of data from the second optical data element are simultaneous.

8. The method of claim 6, wherein the transmission of optical data to the second optical data element and the receiving of data from the second optical data element are time-multiplexed.

9. The method of claim 6, wherein the transmission of optical data to the second optical data element and the receiving of data from the second optical data element are frequency-multiplexed onto two different optical wavelengths, one for transmit and one for receive.

10. The method of claim 1, wherein the power transmission element is an RF power transmission element, and the providing step further provides an optical power transmission element on the robotic manipulator.

11. The method of claim 1, wherein the first optical data element comprises a light pipe or fiber optic element disposed in the first coil center, wherein said light pipe or fiber optic element is optically coupled to a light emitter.

12. The method of claim 1, wherein the second optical data element comprises a light pipe or fiber optic element disposed in the second coil center, wherein said light pipe or fiber optic element is optically coupled to a light detector.

13. The method of claim 1, wherein the surgical device includes a surgical instrument shaft and end effector and a motor, and wherein wirelessly transmitting power from the power transmission element to the wireless power receiving element to operate a function of the surgical device powers the motor to cause operation of the surgical device.

14. The method system of claim 13, wherein the operation of the surgical device is at least one of jaw open, jaw close, articulation or bending in at least one degree of freedom, and instrument tip or shaft roll.

15. The method of claim 13, wherein the surgical device includes a plurality of motors operative to drive a plurality of operations of the surgical device, each motor in electrical communication with the first coil.

16. The method of claim 13, wherein the plurality of operations includes jaw open, jaw close, and articulation or bending in at least one degree of freedom.

17. The method of claim 16 wherein the plurality of operations includes jaw open, jaw close, and instrument tip or shaft roll.

18. The method of claim 11, further including positioning a sterile drape between the robotic arm and the surgical device.

* * * * *